US00PP12907P2

(12) United States Plant Patent
Janson

(10) Patent No.: US PP12,907 P2
(45) Date of Patent: Sep. 3, 2002

(54) ASCLEPIAS PLANT NAMED 'BEATRIX'

(76) Inventor: Nicolaas Johannes Stephanus Janson, Achterweg Zuid 45, 2161 DX Lisse (NL)

( * ) Notice: Subject to any disclaimer, the term of this patent is extended or adjusted under 35 U.S.C. 154(b) by 0 days.

(21) Appl. No.: 09/473,568

(22) Filed: Dec. 29, 1999

(51) Int. Cl.[7] ..... A01H 5/00

(52) U.S. Cl. ..... Plt./263

(58) Field of Search ..... Plt./263

(56) References Cited

PUBLICATIONS

UPOV–ROM GTI JOUVE Retrieval Software, 2000/04 disc, citations for 'Beatrix', Aug. 2000.*

* cited by examiner

*Primary Examiner*—Bruce R. Campell
*Assistant Examiner*—Wendy C. Baker
(74) *Attorney, Agent, or Firm*—C. A. Whealy

(57) ABSTRACT

A distinct cultivar of Asclepias plant named 'Beatrix', characterized by its large orange flowers; uniform flowering within the inflorescence; tolerance to low light conditions; attractive leaves and flower buds; and good post-production longevity.

1 Drawing Sheet

BACKGROUND OF THE INVENTION

The present invention relates to a new and distinct cultivar of Asclepias plant, botanically known as *Asclepias L.*, and hereinafter referred to by the cultivar name Beatrix.

The new Asclepias is a product of a planned breeding program conducted by the Inventor in Lisse, The Netherlands. The new Asclepias originated from a cross made by the Inventor of two unidentified selections of *Asclepias L.*. The new Asclepias was selected on the basis of its flower color, large flower size and uniform flowering.

Asexual reproduction of the new cultivar by terminal cuttings taken at Lisse, The Netherlands, has shown that the unique features of this new Asclepias are stable and reproduced true to type in successive generations.

SUMMARY OF THE INVENTION

Plants of the cultivar Beatrix have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Beatrix'. These characteristics in combination distinguish 'Beatrix' as a new and distinct cultivar:

1. Large orange flowers.
2. Uniform flowering within the inflorescence.
3. Tolerant to low light conditions.
4. Attractive leaves and flower buds.
5. Good post-production longevity.

Plants of the cultivar Beatrix can be compared to plants of the cultivar Tuberosa, not patented. However in side-by-side comparisons conducted in Lisse, The Netherlands, plants of the cultivar Beatrix differed from plants of the cultivar Tuberosa in the following characteristics:

1. Plants of the new Asclepias have larger flowers and larger inflorescences than plants of the cultivar Tuberosa.

2. Plants of the new Asclepias flower more uniformly than plants of the cultivar Tuberosa.
3. Plants of the new Asclepias are more tolerant to low light conditions than plants of the cultivar Tuberosa.
4. Plants of the new Asclepias have larger leaves than plants of the cultivar Tuberosa.
5. Plants of the new Asclepias have better post-production longevity than plants of the cultivar Tuberosa.

Plants of the cultivar Beatrix can be compared to plants of the cultivar Incarnata, not patented. However in side-by-side comparisons conducted in Lisse, The Netherlands, plants of the cultivar Beatrix differed from plants of the cultivar Incarnata in the following characteristics:

1. Plants of the new Asclepias have large orange-colored flowers whereas plants of the cultivar Incarnata have small purple and white-colored flowers.
2. Plants of the new Asclepias have larger inflorescences than plants of the cultivar Incarnata.
3. Plants of the new Asclepias flower more uniformly than plants of the cultivar Incarnata.
4. Plants of the new Asclepias are more tolerant to low light conditions than plants of the cultivar Incarnata.
5. Plants of the new Asclepias have better post-production longevity than plants of the cultivar Incarnata.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Asclepias.

The photograph at the top of the sheet comprises a side perspective view of typical cut flowering stems of 'Beatrix'.

The photograph at the bottom of the sheet comprises a close-up views of typical flower buds, open flowers and leaves of 'Beatrix'.

DETAILED BOTANICAL DESCRIPTION

The following observations, measurements and values describe plants of the new cultivar grown as cut flowers in Lisse, The Netherlands during the late summer under conditions which closely approximate commercial production practice in a glass-covered greenhouse during the spring and summer with day temperatures ranging from 25 to 30° C. and minimum night temperatures of 18° C. Plants used for the description were about five months old.

Color references are made to The Royal Horticultural Society Colour Chart except where general terms of ordinary dictionary significance are used.

Botanical classification: *Asclepias L.* cultivar Beatrix.

Parentage:

*Female parent.*—Unidentified selection of *Asclepias L.*

*Male parent.*—Unidentified selection of *Asclepias L.*

Propagation:

*Type cutting.*—Cuttings.

*Root description.*—Fine, fibrous.

Plant description:

*Form.*—Upright flowering perennial.

*Usage.*—Appropriate for cut flowers.

*Vigor.*—Moderate.

*Plant height.*—About 65 cm.

*Plant width.*—About 40 cm.

*Cut flower length.*—About 1.5 meters.

*Lateral branches.*—Diameter: About 6 mm. Internode length: About 9 cm. Strength: Flexible, but strong. Texture: Very fine short hairs. Color: 146A to 146B.

*Foliage description.*—Leaves simple, generally symmetrical and long persisting. Leaf arrangement opposite. Quantity per lateral branch: Typically more than 40; dense bushy plants. Length: About 16.25 cm. Width: About 5.5 cm. Shape: Lanceolate. Apex: Acute to acuminate. Base: Obtuse. Margin: Entire. Texture: Leathery; very fine short hairs, denser on lower surface. Color: Young foliage, upper surface: Darker than 146A. Young foliage, lower surface: 146A. Mature foliage, upper surface: Close to 147A. Mature foliage, lower surface: 146A to 146B. Petiole: Length: About 7.5 mm. Diameter: About 4 mm. Color: Slightly lighter than 146D.

Flower description:

*Flower type and habit.*—Large single orange flowers arranged in axillary umbels. Flowers face upright. Flowers persistent. Flowering continuous.

*Natural flowering season.*—Spring through fall.

*Inflorescence height.*—About 5 cm.

*Inflorescence diameter.*—About 8.5 cm.

*Number of open flowers per umbel.*—About 6.

*Number of umbels per flowering stem.*—About 4 or 5.

*Fragrance.*—Flowers, none detected; foliage, leather-like odor.

*Flower longevity as a cut flower.*—About 9 days without silver thiosulfate treatment.

*Flower size.*—About 3.9 by 3.9 cm.

*Flower height (depth).*—About 1.3 cm.

*Flower arrangement/appearance.*—Bisexual; calyx five-lobed subtending 5-lobed corolla; staminal corona, single whorl, five-lobed, cuculate, each lobe with a horn.

*Petals.*—Length: About 1.9 cm. Diameter: About 7 mm. Shape: Elliptic. Apex: Acute to acuminate. Margin: Entire. Texture: Smooth. Color: Opened flower, upper surface: Center, 28A; 169B towards margin and apex. Fading to 169B to 169C. Opened flower, lower surface: 19A.

*Sepals.*—Length: About 1.2 cm. Diameter: About 2 mm. Shape: Linear. Apex: Acuminate. Margin: Entire. Texture: Pubescent. Color: Upper surface: 144A to 144B. Lower surface: 144A.

*Corona.*—Length: About 7.5 mm. Diameter: About 3 mm. Texture: Waxy. Color: 28A fading to yellow, 14A.

*Peduncle.*—Strength: Strong. Angle: Upright. Length: About 2.75 cm above leaves to pedicels. Diameter: About 3 mm. Color: 144A to 146A.

*Pedicel.*—Strength: Strong. Angle: About 30 to 45° to vertical. Length: About 3 cm. Diameter: About 1.5 mm. Color: 144A.

*Reproductive organs.*—Stamens: Stamen number: About five with two anthers each. Anther shape: Oblong, winged. Anther length: About 1.5 mm. Anther color: 146A. Pollen amount: Not observed. Pistils: Two superior ovaries with one common stigma.

*Seed.*—Seed production has not been observed.

Disease resistance: Resistance to pathogens common to Asclepias has not been observed.

Low light tolerance: Plants of the new Asclepias will continue to flower under periods of low light in the autumn. In Northwestern Europe, typically flower buds of plants of other known cultivars of *Asclepias L.* will abscise about mid-September when light levels decrease, however flower buds of the new Asclepias do not abscise until the first or second week of October.

It is claimed:

1. A new and distinct cultivar of Asclepias plant named 'Beatrix', as illustrated and described.

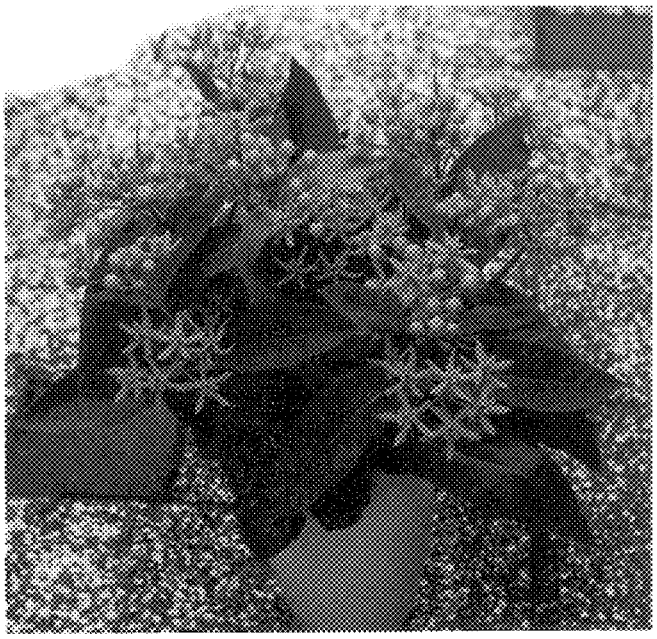
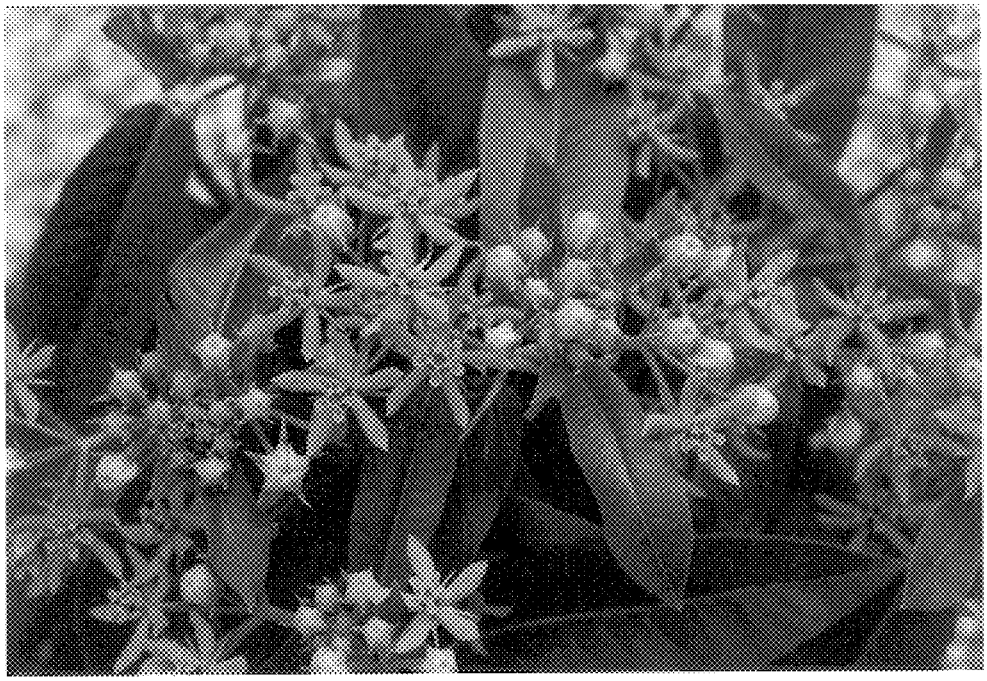

* * * * *